United States Patent [19]

Starks

[11] 4,042,631

[45] Aug. 16, 1977

[54] TELOMERS FROM β-DIKETONES AND VINYL CHLORIDE

[75] Inventor: Charles M. Starks, Ponca City, Okla.

[73] Assignee: Continental Oil Company, Ponca City, Okla.

[21] Appl. No.: 566,544

[22] Filed: Apr. 9, 1975

[51] Int. Cl.$^2$ ............................................... C07C 49/76
[52] U.S. Cl. ........................... 260/593 H; 260/590 R; 260/590 D; 106/75
[58] Field of Search .......... 260/92.8 R, 593 H, 593 R, 260/594, 590 D, 590 E, 590 R

[56] References Cited

U.S. PATENT DOCUMENTS

| 2,306,765 | 12/1942 | Stilles | 260/594 |
|---|---|---|---|
| 2,447,626 | 7/1948 | Bahner | 260/593 R |
| 2,864,850 | 12/1958 | Westfahl | 260/593 R |
| 3,557,244 | 7/1971 | Schrage | 260/92.8 R |

OTHER PUBLICATIONS

Kirk–Othmer, Encyclopedia of Chem. Technology, vol. 21, pp. 369–373, (1970).

*Primary Examiner*—James O. Thomas, Jr.
*Assistant Examiner*—James H. Reamer
*Attorney, Agent, or Firm*—Bayless E. Rutherford, Jr.

[57] ABSTRACT

β-diketones having two ketone groups bonded to a common carbon atom which is bonded to at least one hydrogen atom, such as 2,4-pentanedione, are reacted with vinyl chloride to form telomers.

10 Claims, No Drawings

TELOMERS FROM β-DIKETONES AND VINYL CHLORIDE

BACKGROUND OF THE INVENTION

This invention relates to certain novel telomers and to a process for producing such telomers. In one aspect, the present invention relates to a process for producing telomers by contacting vinyl chloride with β-diketones wherein said β-diketones have two ketone groups bonded to a common carbon atom and wherein said carbon atom is further bonded to at least one hydrogen atom.

Telomerization reactions wherein taxogens are reacted with telogens have been known for many years. Numerous patents have been issued in the field of telomers, said patents describing various types of utility for these materials. The prior art patents teach that telomers are useful as solvents, plasticizers, wax substitutes, and heat transfer media. Illustrative of such prior art patents is U.S. Pat. No. 3,839,474 which discloses that dichlorobutenes such as 3,4-dichloro-1-butene and 1,4-dichloro-2-butene react with vinyl chloride to form telomers which are polyhalogenated alkenes. However, in the prefiling search, no relevant patents were located which suggested the use of βdiketones as telogens in a telomerization reaction with vinyl chloride.

OBJECTS OF THE INVENTION

An object of the invention is to provide a process for producing telomers. Another object of the invention is to provide a process for producing telomers by reacting β-diketones with vinyl chloride. Still another object of the invention is to provide telomers, produced by reacting β-diketones with vinyl chloride, as compositions of matter which are particularly useful as coatings and water-proofing agents.

SUMMARY OF THE INVENTION

Briefly, the present invention relates to a process for the production of telomers by reacting vinyl chloride with β-diketones, said β-diketones having two ketone groups bonded to a carbon atom which is bonded to at least one hydrogen atom.

In another aspect, the present invention relates to telomers of the type described in the immediate foregoing as compositions of matter.

DESCRIPTION OF THE PREFERRED EMBODIMENTS

The instant invention relates to telomers prepared by the telomerization of vinyl chloride and β-diketones and to the production of said telomers. The term β-diketones, as employed herein, is to be understood to be compounds which are characterized as having two ketone groups bonded to a common carbon atom which is bonded to at least one hydrogen atom. Such β-diketones are typically represented by the general formula:

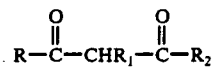

wherein R and $R_2$ can be alkyl radicals containing from 1 to about 20 carbon atoms, aromatic radicals containing 6 to 10 carbon atoms, such as phenyl and naphthyl, or alkyl-substituted aromatic radicals, wherein the alkyl constituent contains from 1 to about 6 carbon atoms and wherein the aromatic moiety is phenyl or naphthyl, wherein $R_1$ can be hydrogen, alkyl radicals containing from 1 to about 20 carbon atoms, or halogen-substituted alkyl radicals containing 1 to about 20 carbon atoms and wherein the halogen is chlorine, bromine, or fluorine, but preferably is chlorine. The alkyl radicals can be of a linear or branched configuration.

The reaction which takes place in the production of telomers by the process of the present invention can be represented as follows:

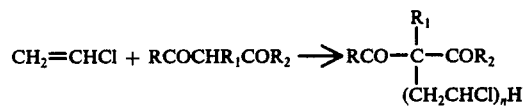

wherein R, $R_1$, and $R_2$ are as previously defined, and n is an integer of from 1 to about 200. Telomer products of the type defined having molecular weights in the range of about 600 to about 1600, preferably about 750 to about 850, are very useful in the preparation of high strength silicate foam compositions.

While any suitable β-diketone having two ketone groups attached to a common carbon atom which is likewise attached to at least one hydrogen, as defined above, can be employed, especially desirable results are obtained when the β-diketone constituent is selected from the group consisting of 2,4-pentanedione, alkyl-substituted 2,4-pentanediones, benzoyl acetones, and dibenzoylmethanes. Especially desirable results have been obtained wherein the telomer is produced by the reaction of vinyl chloride with 2,4-pentanedione.

In carrying out the reaction for the production of telomers according to the present invention, the amount of the vinyl chloride and β-diketone employed can vary widely and will depend to a large extent on the desired molecular weight of the resultant product. Generally, however, it has been found desirable to employ from about 0.1 to 20 moles of vinyl chloride for each mole of the β-diketone constituent. Amounts of vinyl chloride outside of this range are not satisfactory to produce telomers having the beneficial properties of the telomers produced according to the invention. Especially desirable results have been obtained when employing from about 0.7 to 2.0 moles of vinyl chloride for each mole of β-diketone.

The telomerization reaction of the invention can be conducted at temperatures in the range of −10° to about 250° C. At temperatures below about −10° C, insufficient rate of reaction occurs to be practical. At temperatures above about 250° C, deleterious side reactions become a problem. Free radical initiating means are employed. Examples of free radical initiating means include chemical, gamma radiation, ultraviolet radiation, and thermal. Of these, chemical, gamma radiation, and ultraviolet radiation are more suitable.

Knowing that free radical initiating means are used and knowing the temperatures under which the reaction is conducted, any person skilled in the art can readily determine the type of initiating means and the optimum temperature for that particular means.

When chemical free radical initiating means are employed, for optimum results a temperature of 50° to 150° C is considered suitable. When thermal initiation is employed, preferably the temperature is in the range of above 150° C to about 250° C.

Examples of suitable chemical free radical initiators include organic peroxides such as benzoyl peroxide, acetyl peroxide, t-butyl peroxide, t-butyl peracetate, ethyl peroxide, t-butyl perbenzoate, succinic peroxide, diisopropyl percarbonate, and the like as well as azobisisobutrylniltrile, other azo compounds, triphenylchloromethane, copper oxides, iron oxides, chromium, tetraethyl lead, and the like.

Pressure is not critical according to this invention. In general, any pressure sufficient to maintain the vinyl chloride and the β-diketone in a fluid reaction environment can be employed. Pressures in the range of 0 to 2,000 psig are suitable. Presently, it is preferred to employ pressures in the range of 0 to 200 psig for optimum results. It is often convenient to operate at atmospheric pressure.

A sufficient reaction time is employed to carry out the degree of conversion desired. Reaction time is determined by the rate of initiation provided by initiator, and optimum reaction time can be determined by simple experiment for each particular system. Reaction times from about 2 minutes to 10 days are exemplarily employed.

If desired, diluents can be employed in the reaction environment. Examples of some suitable diluents include hydrocarbons such as benzene, toluene, xylene, and the like. Halogenated hydrocarbons such as 1,2-dichlorotetrafluoroethane, chlorotrifluoromethane, dichlorodifluoromethane, chlorobenzene, and the like can be employed if desired. If a diluent is employed, it can comprise as much as 95 weight percent of the fluid materials present in the reaction environment.

When a chemical free radical initiating means is employed, about 0.001 to 0.10 moles of the chemical free radical forming initiator per mole of vinyl chloride is often suitable.

The telomers produced according to this invention can be separated from the diluent and from other materials present by any means known to the art for separation of organic chemicals. For example, fractional distillation, fractional crystallization, selective solvents chromatography, and the like can be employed. The telomer products produced are not pure compounds but rather a mixture of products.

The following examples are presented so that the invention may be more readily understood. The examples should not be interpreted to limit the invention in any manner.

EXAMPLE 1

A series of experiments were conducted to produce telomers from vinyl chloride and 2,4-pentanedione as the β-diketone; vinyl chloride, solvent, and benzoyl peroxide (initiator) were charged to a stirred reactor. The reactor was a thick-walled glass reactor vessel which upon charging of the reaction mixture was sealed. The reaction mixture was then placed in an oil vat at 60° to 70° C at atmospheric pressures for 24 hours. After cooling and venting, hexane was added to precipitate the telomer product. The telomer product was then dried and its molecular weight determined.

Telomer products having generic formulas as shown hereinbefore in this application were obtained in each run. Further details of the process and the product results are shown in the table which follows.

Table 1

| Run No. | Charge to Reactor | | Telogen[2] Weight (g.) | Telomer Product | | |
|---|---|---|---|---|---|---|
| | $C_6H_6$ (ml.) | $B_xO_x$[1] (g.) | | Vinyl Chloride (g.) | Weight (g.) | Average Molecular Weight |
| 1 | 43.2 | 0.18 | 38.6 | 47.0 | 14.2 | 778 |
| 2 | 46.9 | 0.35 | 20.77 | 39.9 | 19.8 | 796 |
| 3 | 43.6 | 0.32 | 9.60 | 36.7 | 22.6 | 1507 |

1. $B_xO_n$ is benzoyl peroxide
2. 2,4-pentanedione

The above example clearly demonstrates the production of telomers from vinyl chloride and β-diketones wherein said β-diketones are characterized as having two ketone groups bonded to a common carbon atom which is likewise bonded to at least one hydrogen atom.

The telomers produced in Example 1 were then admixed with sodium silicate foam ingredients prior to the addition of the surfactant components of the foam ingredient, and it was determined that the telomer substantially increased the compressive strength of the foam. Thus, the telomers of the present invention can readily be employed to improve and strengthen sodium silicate foam when such are incorporated into the silicate foam prior to the addition of the surfactant constituent in the formation of said foam.

It is to be understood that the present invention is restricted to the novel telomers disclosed herein and to the preparation of these telomers. Silicate foam compositions containing the telomers of my invention are disclosed and claimed in application Ser. No. 566,550 filed Apr. 9, 1975 and now U.S. Pat. No. 3,961,972, entitled "High Strength Silicate Foam And Method For Producing Same," of which the inventors are Derry D. Sparlin and Charles M. Starks.

Having thus described the invention, I claim:

1. Vinyl chloride telomers having the formula $$RCO-CR_1-COR_2$$
$$|$$
$$(CH_2-CHCl)_nH$$

wherein R and $R_2$ are selected from the group consisting of alkyl radicals containing from 1 to about 20 carbon atoms, aromatic radicals containing 6 to 10 carbon atoms, and alkyl substituted aromatic radicals, wherein the alkyl constituent contains from 1 to about 6 carbon atoms and wherein the aromatic moiety is phenyl or naphthyl; wherein $R_1$ is selected from the group consisting of hydrogen, alkyl radicals containing from 1 to about 20 carbon atoms, and halogen substituted alkyl radicals containing 1 to about 20 carbon atoms and wherein the halogen is chlorine, bromine, or fluorine; and $n$ is an integer of from 1 to about 200.

2. The vinyl chloride telomer of claim 1 wherein R and $R_2$ are methyl radicals, $R_1$ is hydrogen, and $n$ is from 1 to about 50.

3. A process for producing vinyl chloride telomers, said telomers being represented by the formula $$RCO-CR_1-COR_2$$
$$|$$
$$(CH_2-CHCl)_nH$$

wherein R and $R_2$ are selected from the group consisting of alkyl radicals containing from 1 to about 20 carbon atoms, aromatic radicals containing 6 to 10 carbon atoms, and alkyl substituted aromatic radicals, wherein the alkyl constituent contains from 1 to about 6 carbon atoms and wherein the aromatic moiety is phenyl or naphthyl; wherein $R_1$ is selected from the group consisting of hydrogen, alkyl radicals containing from 1 to about 20 carbon atoms, and halogen substituted alkyl radicals containing 1 to about 20 carbon atoms and wherein the halogen is chlorine, bromine, or fluorine; and n is an integer of from about 1 to about 200.

said process comprising contacting a β-diketone compound with from about 0.1 to about 20 moles of vinyl chloride per mole of β-diketone compound using free radical initiating means at a temperature in the range of about −10° C to about 250° C and a pressure of from about 0 to about 2,000 psig, and thereafter recovering from the mixture the desired telomer product, said process being characterized further in that said β-diketone is represented by the general formula

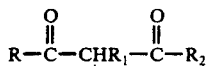

wherein R, $R_1$, $R_2$, are the same as defined in connection with said telomers.

4. The process of claim 3 wherein said reaction is conducted employing from about 0.001 to 0.10 moles of a chemical free radical initiator per mole of vinyl chloride at a temperature of about 50 to about 150° C and at a pressure of from 0 to 200 psig.

5. The process of claim 4 wherein from about 0.7 to 2.0 moles of vinyl chloride are employed per mole of β-diketone and said β-diketone constituent is selected from the group consisting of 2,4-pentanedione, alkyl substituted 2,4-pentanediones, benzoyl acetones and dibenzoylmethanes.

6. The process of claim 4 wherein the chemical free radical initiator is selected from the group consisting of benzoyl peroxide, di-t-butyl peroxide sulfuryl chloride, t-butyl hypochlorite and azobisisisobutyronitrile.

7. The process of claim 3 wherein it is initiated thermally using a temperature in the range of above 150° C to about 250° C.

8. The process of claim 4 wherein up to about 95 percent by weight of a hydrocarbon diluent is employed, said diluent being based on the total weight of the reaction mixture.

9. The process of claim 4 wherein up to about 95 percent by weight of a halogenated hydrocarbon diluent is employed, said diluent being based on the total weight of the reaction mixture.

10. The process of claim 8 wherein the hydrocarbon diluent is a monocyclic aromatic hydrocarbon.

* * * * *